US012582495B2

(12) United States Patent (10) Patent No.: US 12,582,495 B2
Danno et al. (45) Date of Patent: Mar. 24, 2026

(54) COVER FOR OCCLUSAL FORCE METER

(71) Applicant: Murata Manufacturing Co., Ltd.,
Nagaokakyo (JP)

(72) Inventors: Keisuke Danno, Nagaokakyo (JP);
Toru Yabe, Nagaokakyo (JP)

(73) Assignee: MURATA MANUFACTURING CO.,
LTD., Nagaokakyo (JP)

( * ) Notice: Subject to any disclaimer, the term of this
patent is extended or adjusted under 35
U.S.C. 154(b) by 286 days.

(21) Appl. No.: 18/364,597

(22) Filed: Aug. 3, 2023

(65) Prior Publication Data

US 2023/0372047 A1 Nov. 23, 2023

Related U.S. Application Data

(63) Continuation of application No.
PCT/JP2022/007586, filed on Feb. 24, 2022.

(30) Foreign Application Priority Data

Mar. 5, 2021 (JP) ................................. 2021-035825

(51) Int. Cl.
*A61B 50/00* (2016.01)
*A61B 5/22* (2006.01)
*G01L 1/14* (2006.01)
(52) U.S. Cl.
CPC .............. *A61B 50/00* (2016.02); *A61B 5/228*
(2013.01); *G01L 1/142* (2013.01); *A61B*
*2050/005* (2016.02); *A61B 2562/0247*
(2013.01)
(58) Field of Classification Search
CPC ... A61B 50/00; A61B 5/228; A61B 2050/005;
A61B 2562/0247; A61B 2562/0261;
A61B 2562/16; G01L 1/142

USPC ...................................................... 73/862.626
See application file for complete search history.

(56) References Cited

U.S. PATENT DOCUMENTS

2011/0280378 A1* 11/2011 Feltz .................... A61B 6/4435
378/191
2021/0259630 A1 8/2021 Shimuta et al.

FOREIGN PATENT DOCUMENTS

| JP | H08252245 A | 10/1996 |
|----|-------------|---------|
| JP | H0966048 A | 3/1997 |
| JP | 2013195118 A | 9/2013 |
| JP | 2015188484 A * | 11/2015 |
| JP | 2020068892 A | 5/2020 |
| JP | 2020195776 A * | 12/2020 |
| JP | 2022007973 A | 1/2022 |

OTHER PUBLICATIONS

Translation of JP-2015188484-A (Year: 2015).*
Translation of JP-2020195776-A (Year: 2020).*
International Search Report in PCT/JP2022/007586, mailed Apr. 19, 2022, 3 pages.

* cited by examiner

*Primary Examiner* — Nathaniel T Woodward
(74) *Attorney, Agent, or Firm* — ArentFox Schiff LLP

(57) ABSTRACT

A cover for an occlusal force meter, the cover including: a
cover main body that covers a pressure sensor of the occlusal
force meter, the cover main body having a bag shape; and an
elastic body attached to an outer surface of the cover main
body, wherein a Young's modulus of a material of the cover
main body is larger than a Young's modulus of a material of
the elastic body, and a rubber hardness of the elastic body is
equal to or less than E15.

17 Claims, 3 Drawing Sheets

COVER FOR OCCLUSAL FORCE METER

CROSS REFERENCE TO RELATED APPLICATIONS

The present application is a continuation of International application No. PCT/JP2022/007586, filed Feb. 24, 2022, which claims priority to Japanese Patent Application No. 2021-035825, filed Mar. 5, 2021, the entire contents of each of which are incorporated herein by reference.

TECHNICAL FIELD

The present disclosure relates to a cover for an occlusal force meter.

BACKGROUND ART

In Patent Document 1, an occlusal force meter that measures the occlusal force of maxillary and mandibular teeth is disclosed. The occlusal force meter includes a pressure sensor. During measurement, the occlusal force meter is used while the pressure sensor is covered with a cover. The occlusal force meter detects pressure when the pressure sensor is bitten by teeth as occlusal force.

Patent Document 1: Japanese Unexamined Patent Application Publication No. 9-66048

SUMMARY OF THE INVENTION

When the occlusal force meter disclosed in Patent Document 1 is used, in some cases, the pressure sensor is covered with a cover. In this case, if the hardness of the cover is large, the teeth may be damaged by the cover when the pressure sensor is bitten. On the other hand, if the hardness of the cover is small, a hole may be formed in the cover, for example, when the occlusal force meter is inserted into the cover, and saliva and the like in the oral cavity may enter the cover.

To solve the above problem, an aspect of the present disclosure provides a cover for an occlusal force meter that includes: a cover main body that covers a pressure sensor of the occlusal force meter, the cover main body having a bag shape; and an elastic body attached to an outer surface of the cover main body, wherein a Young's modulus of a material of the cover main body is larger than a Young's modulus of a material of the elastic body, and a rubber hardness of the elastic body is equal to or less than E15.

According to the above configuration, the cover main body and the elastic body can cover the pressure sensor. The rubber hardness of the elastic body is equal to or less than E15 and is appropriately small. Therefore, when the pressure sensor is bitten during measurement of the occlusal force, the elastic body acts as a cushioning material and can reduce the impact on the teeth. In addition, the Young's modulus of the material of the cover main body is larger than the Young's modulus of the material of the elastic body. Since the cover main body has an appropriate hardness, the cover main body is less likely to be damaged.

According to an aspect of the present disclosure, while the teeth can be prevented from being damaged by the cover for an occlusal force meter, damage to the cover main body can be reduced.

DETAILED DESCRIPTION OF THE PREFERRED EMBODIMENTS

Hereinafter, an embodiment of a cover for an occlusal force meter will be described. First, an occlusal force meter to which the cover for an occlusal force meter of the present embodiment is applied will be described. Note that for the sake of easy understanding, the accompanying drawings may illustrate components in an enlarged manner. In addition, the dimensional ratios of the components may differ from the dimensional ratios of actual components or the dimensional ratios of the components in other drawings.

<Occlusal Force Meter>

Figure 1:
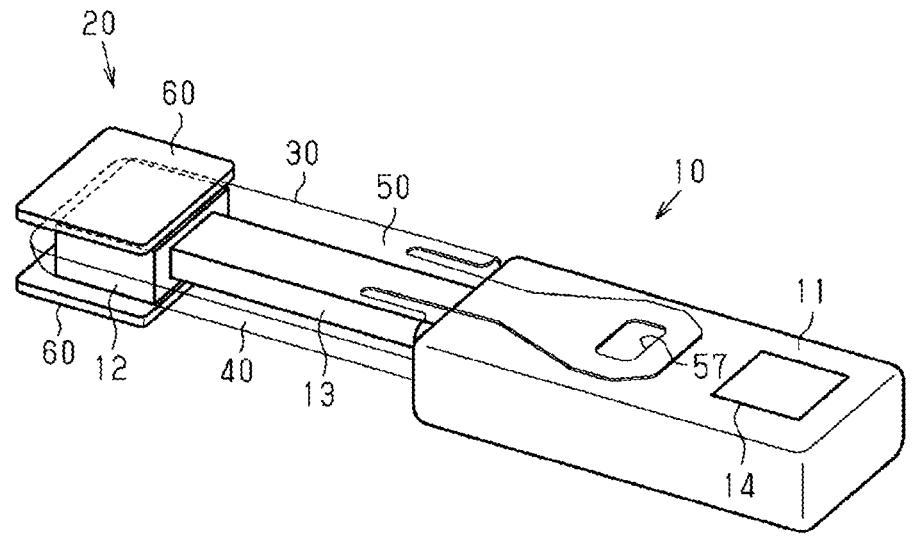
FIG. 1 is a perspective view of a cover attached to an occlusal force meter.

As illustrated in FIG. 1, an occlusal force meter 10 includes a handle 11, a pressure sensor 12, an arm 13, and a display 14.

The occlusal force meter 10 has a bar shape as a whole. The handle 11 constitutes substantially half of the occlusal force meter 10 on one side in a longitudinal direction. The handle 11 has a substantially rectangular parallelepiped shape. The handle 11 is gripped by a user when an occlusal force is measured.

The arm 13 is connected to an end surface of the handle 11 on another side in the longitudinal direction. The arm 13 has a flat prism shape. The arm 13 extends in substantially the same direction as the handle 11. The arm 13 is thinner than the handle 11.

The pressure sensor 12 is connected to an end of the arm 13 on an opposite side from the handle 11 in the longitudinal direction. That is, the pressure sensor 12 is located at a leading end of the occlusal force meter 10. The pressure sensor 12 has a substantially rectangular parallelepiped shape.

Figure 2:
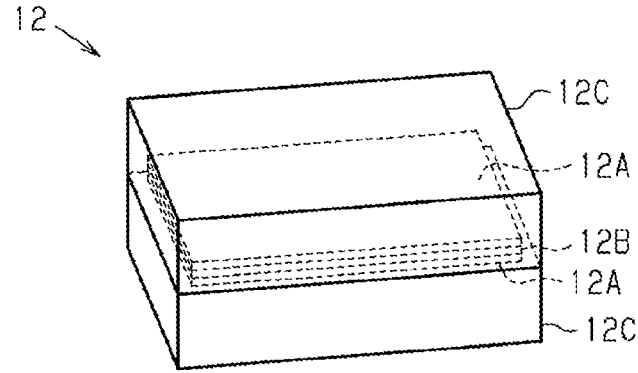
FIG. 2 is an enlarged see-through view of a pressure sensor.

As illustrated in FIG. 2, the pressure sensor 12 has a pair of plate materials 12A, a first resin material 12B, and a pair of second resin materials 12C. The material of the pair of plate materials 12A is a conductive metal. Each plate material 12A has a rectangular shape in a plan view thereof. The main surfaces of the pair of plate materials 12A face each other. The pair of plate materials 12A is connected to wiring (not illustrated). The pair of plate materials 12A functions as electrodes of a capacitor.

The first resin material 12B is located between the main surfaces of the pair of plate materials 12A. That is, the first resin material 12B fills a gap between the pair of plate materials 12A. The first resin material 12B is a plate material. In the plan view, the first resin material 12B has a rectangular shape, which is the same as the main surface of each plate material 12A. When viewed in a direction orthogonal to the main surfaces of the plate materials 12A, the first resin material 12B overlaps with the plate materials 12A without protruding from the plate materials 12A.

Each second resin material 12C is located on an opposite side from the first resin material 12B with respect to the plate material 12A. One second resin material 12C exists for one plate material 12A. That is, one second resin material 12C is located on a side opposite to the main surface of one plate material 12A. Another second resin material 12C is located on a side opposite to the main surface of another plate material 12A. That is, the pair of plate materials 12A is sandwiched between the pair of second resin materials 12C. Each second resin material 12C has a substantially rectangular parallelepiped shape.

As illustrated in FIG. 1, the display 14 is located in the handle 11. A display surface of the display 14 is exposed to the outside of the handle 11. The display 14 displays information of pressure detected by the pressure sensor 12 and the like.

<Cover>

As illustrated in FIG. 1, a cover for an occlusal force meter (hereinafter, simply referred to as a cover 20) covers the pressure sensor 12 and the arm 13 of the occlusal force meter 10.

Figure 3:
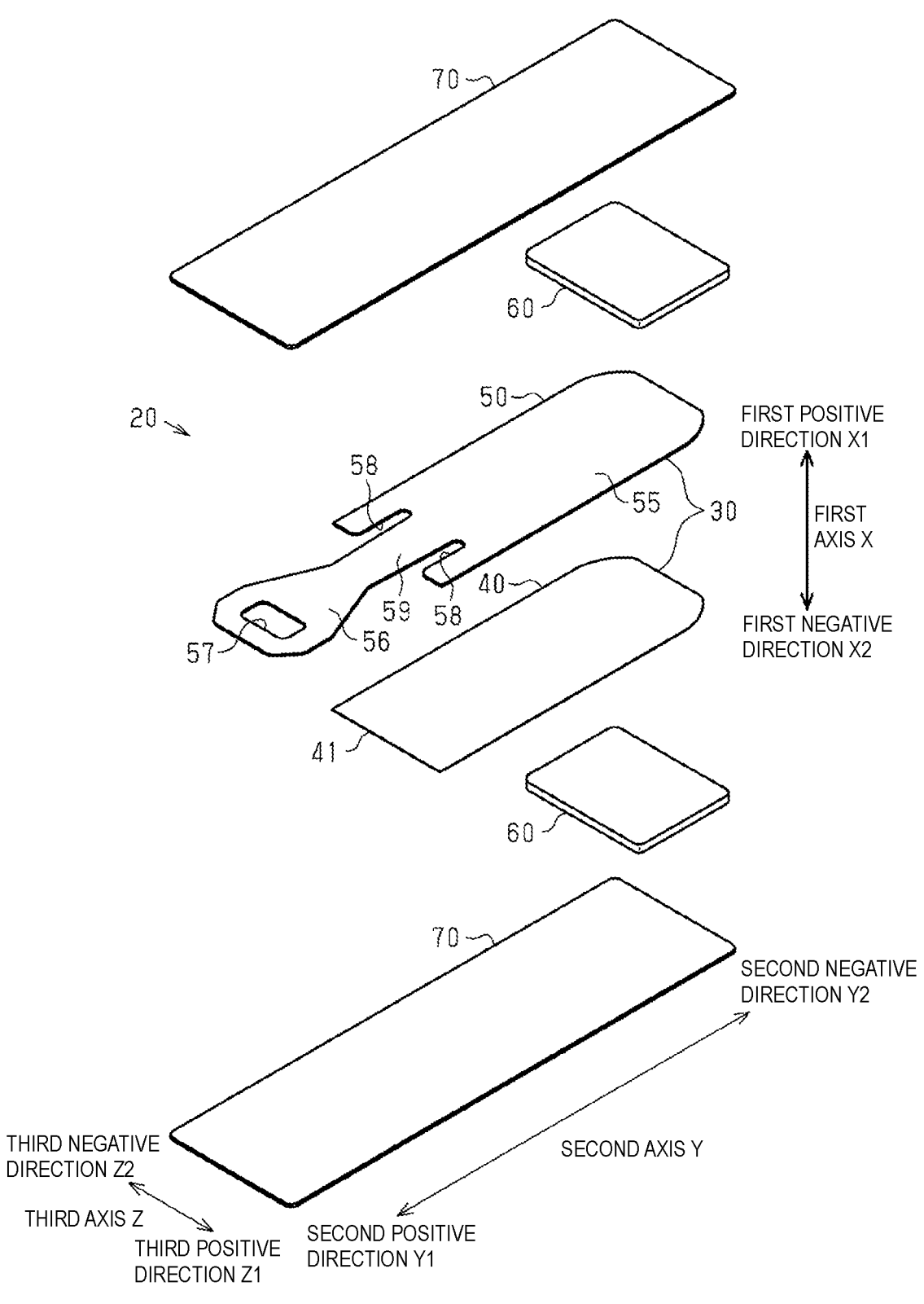
FIG. 3 is an exploded perspective view of the cover.

As illustrated in FIG. 3, the cover 20 includes a cover main body 30, for covering the pressure sensor 12, that has a bag shape and elastic bodies 60 attached to outer surfaces of the cover main body 30.

The cover main body 30 includes a first sheet 40 and a second sheet 50 facing the first sheet 40. The first sheet 40 has a substantially rectangular shape. Note that in the following description, the first sheet 40 is planar unless otherwise stated. In addition, when the first sheet 40 is planar, a first axis X is an axis orthogonal to the first sheet 40. In addition, a second axis Y is an axis orthogonal to the first axis X and along which a long side of the first sheet 40 extends. In addition, a third axis Z is an axis orthogonal to both of the first axis X and the second axis Y. Note that one of two directions extending along the first axis X is a first positive direction X1, and a direction opposite to the first positive direction X1 is a first negative direction X2. In addition, one of two directions extending along the second axis Y is a second positive direction Y1, and a direction opposite to the second positive direction Y1 is a second negative direction Y2. In addition, one of two directions extending along the third axis Z is a third positive direction Z1, and a direction opposite to the third positive direction Z1 is a third negative direction Z2.

As illustrated in FIG. 3, an edge 41 of the first sheet 40 in the second positive direction Y1 linearly extends. In addition, each corner of the first sheet 40 in the second positive direction Y1 has a right angle. On the other hand, each corner portion of the first sheet 40 in the second negative direction Y2 is rounded. The material of the first sheet 40 is a synthetic resin and is, for example, polyethylene terephthalate (PET) or the like.

The second sheet 50 is located on the first positive direction X1 side when viewed from the first sheet 40. The shape of the second sheet 50 as a whole is elongated along the second axis Y.

Figure 4:
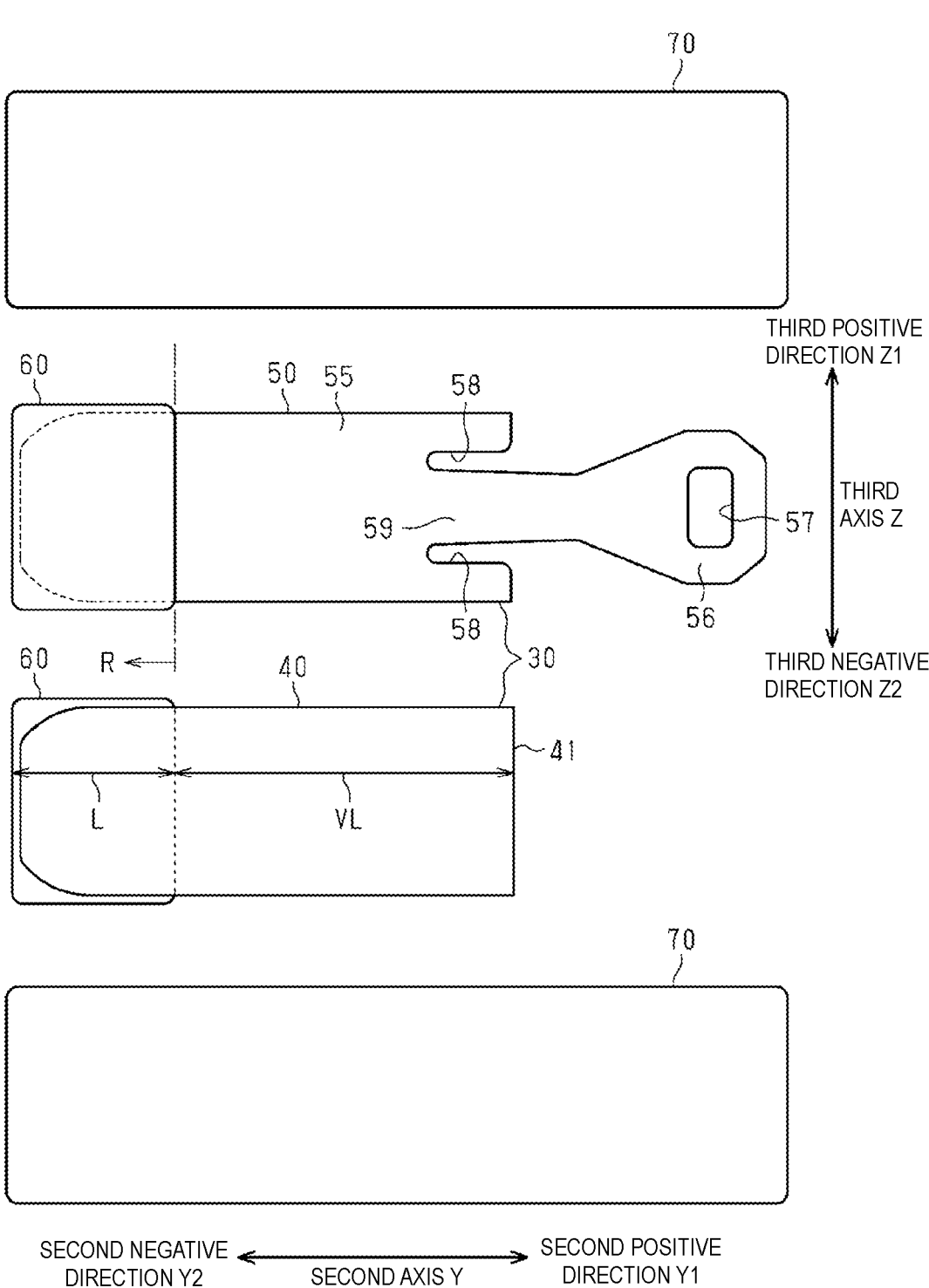
FIG. 4 is an exploded plan view of the cover.

As illustrated in FIG. 4, the second sheet 50 includes a base 55, a projecting portion 56, two slits 58, and a lift-up portion 59. The base 55 has a substantially rectangular shape. The dimension of the base 55 along the second axis Y coincides with the dimension of the first sheet 40 along the second axis Y. The dimension of the base 55 along the third axis Z coincides with the dimension of the first sheet 40 along the third axis Z. In addition, each corner portion of the base 55 in the second negative direction Y2 is rounded similarly to the first sheet 40. That is, the base 55 has substantially the same shape as the first sheet 40 except for the existence of the slits 58 and the lift-up portion 59 described later.

The base 55 of the second sheet 50 overlaps with the first sheet 40. While the base 55 overlaps with the first sheet 40, an outer edge of the base 55 coincides with an outer edge of the first sheet 40. In addition, the base 55 of the second sheet 50 and the first sheet 40 are joined to each other at edges thereof in the second negative direction Y2, edges thereof in the third positive direction Z1, and edges thereof in the third negative direction Z2 of the third axis Z. That is, the cover main body 30 is a flat bag without gussets in which a part of the peripheral edge of the first sheet 40 and a part of the peripheral edge of the second sheet 50 are joined to each other. In addition, the edge 41 of the first sheet 40 constitutes a part of an opening edge of the cover main body 30.

Each slit 58 extends from the edge of the base 55 on the second positive direction Y1 side. The direction in which each slit 58 extends coincides with the second axis Y. That is, the two slits 58 extend parallel to each other. The extending dimensions of the two slits 58 are the same. As described above, the outer edge of the base 55 coincides with the outer edge of the first sheet 40. Therefore, while the first sheet 40 and the second sheet 50 are planar, in the plan view from the first positive direction X1, the slits 58 extending from the edge of the base 55 pass over the edge 41 of the first sheet 40.

The lift-up portion 59 is a region of the second sheet 50 between the two slits 58. The entire lift-up portion 59 including the edge of the lift-up portion 59 in the third positive direction Z1 and the edge of the lift-up portion 59 in the third negative direction Z2 is not joined to the first sheet 40. That is, the entire lift-up portion 59 including both edges in a direction along the third axis Z is not joined to the first sheet 40.

The projecting portion 56 projects from the lift-up portion 59. In other words, the lift-up portion 59 is adjacent to the projecting portion 56 in a direction opposite to the projecting direction of the projecting portion 56. In addition, in the plan view from the first positive direction X1, the projecting portion 56 projects from the edge 41 of the first sheet 40 to the outside of the first sheet 40. Specifically, the projecting portion 56 projects in the second positive direction Y1 from the outer edge of the lift-up portion 59 in the second positive direction Y1. Therefore, the projecting portion 56 and the lift-up portion 59 are continuous to each other. In addition, the lift-up portion 59 is separable from the first sheet 40 together with the projecting portion 56.

The dimension along the third axis Z of the projecting portion 56 at the end on the second negative direction Y2 side is the same as the dimension along the third axis Z of the lift-up portion 59. That is, the dimension along the third axis Z of the end of the projecting portion 56 on the second negative direction Y2 side is the same as the interval between the two slits 58. In addition, as a whole, the dimension along the third axis Z of the projecting portion 56 gradually increases toward the second positive direction Y1.

In addition, the projecting portion 56 has a through-hole 57. The through-hole 57 is located at a position where the dimension of the projecting portion 56 along the third axis Z is large. That is, the through-hole 57 is located near the end portion of the projecting portion 56 on the second positive direction Y1 side. The through-hole 57 has a substantially rectangular shape in the plan view. Note that the material of the second sheet 50 is a synthetic resin and is, for example, PET or the like. In the present embodiment, the materials of the first sheet 40 and the second sheet 50 are the same PET.

As illustrated in FIG. 3, the two elastic bodies 60 are attached to the outer surfaces of the cover main body 30. Specifically, the elastic bodies 60 are attached to the outer surface of the first sheet 40 on the first negative direction X2 side and the outer surface of the second sheet 50 on the first positive direction X1 side. The two elastic bodies 60 each have a flat rectangular parallelepiped shape. In addition, the two elastic bodies 60 have the same shape.

As illustrated in FIG. 4, in the plan view along the first axis X, each side of each elastic body 60 is parallel to the second axis Y or the third axis Z. The dimension of each elastic body 60 in the direction along the second axis Y is smaller than the dimension of the base 55 in the direction along the second axis Y. In addition, the dimension of each elastic body 60 in the direction along the third axis Z is larger than the dimension of the base 55 in the direction along the third axis Z.

Here, as illustrated in FIG. 4, in the plan view along the first axis X, a virtual line segment VL, which is the shortest line from each elastic body 60 to the opening edge of the cover main body 30, is drawn. In the present embodiment, the opening edge of the cover main body 30 coincides with the edge 41 of the first sheet 40. Therefore, the virtual line segment VL is a line segment drawn from the edge 41 of the first sheet 40 to each elastic body 60 and extending parallel to the second axis Y. In addition, when viewed from an end of each elastic body 60 in the second positive direction Y1, all the region of the cover main body 30 on the second negative direction Y2 side is a covered region R. At this time, each elastic body 60 covers the entire covered region R of the cover main body 30.

In addition, the length of the above virtual line segment VL is larger than a maximum dimension L of each elastic body 60 in a direction along the virtual line segment VL. That is, when viewed in a direction along the first axis X, the dimension of the portion of the cover main body 30 protruding from each elastic body 60 along the second axis Y is larger than the dimension of each elastic body 60 in the direction along the second axis Y.

The elastic bodies 60 include a foamed resin. In the present embodiment, the entire elastic bodies 60 are made of a foamed resin. In addition, in the elastic bodies 60, which are made of a foamed resin, open cells connected to the outside of the elastic bodies 60 exist. That is, bubbles existing inside the elastic bodies 60 are connected to each other, and a fluid can enter the inside of the elastic bodies 60 from the outside.

The material of the elastic bodies 60 is a polyolefin-based resin, of which the main monomer is an olefin. More specifically, the material of the elastic bodies 60 is polyethylene, an ethylene-vinyl acetate copolymer, polypropylene, or the like.

The rubber hardness of the material of the elastic bodies 60 is equal to or less than E15. That is, the foaming ratio of the elastic bodies 60 is adjusted such that the rubber hardness is equal to or less than E15. Note that the "rubber hardness" indicates the hardness measured by a type E durometer conforming to JIS K 6253. In addition, when the Young's modulus of the material of the elastic bodies 60 is compared to the Young's modulus of the material of the cover main body 30, the Young's modulus of the material of the cover main body 30 is larger than the Young's modulus of the material of the elastic bodies 60.

The outer surface of the cover main body 30 is more hydrophobic than the elastic bodies 60. That is, PET, which is the material of the first sheet 40 and the second sheet 50, is more hydrophobic than a polyolefin-based resin, which is the material of the elastic bodies 60. Note that comparison of hydrophobicity can be performed by the following test. That is, PET that is the same as the material of the first sheet 40 and the second sheet 50 is formed into a film shape. Similarly, the polyolefin-based resin that is the same as the material of the elastic bodies 60 is formed into a film shape. The same amount of water droplets is dropped to these two test films. Then, the film having a larger angle formed between the film and an outer surface of the water droplet is more hydrophobic.

As illustrated in FIG. 3, the cover 20 includes a protective sheet 70 on an opposite side from the cover main body 30 when viewed from each elastic body 60. That is, the cover 20 includes two protective sheets 70. Each protective sheet 70 is joined to the cover main body 30 and the elastic body 60 so as to be removable. Each protective sheet 70 has a substantially rectangular shape having a larger dimension along the second axis Y. The dimension of each protective sheet 70 in the direction along the second axis Y is larger than the dimension of the second sheet 50 including the projecting portion 56 in the direction along the second axis Y. The dimension of each protective sheet 70 in the direction along the third axis Z is slightly larger than the dimension of the second sheet 50 in the direction along the third axis Z. That is, the overall dimension of the protective sheet 70 is larger than the cover main body 30.

The surface of each protective sheet 70 facing the cover main body 30 has an adhesive force for other sheets. In the present embodiment, the entire surface of each protective sheet 70 facing the cover main body 30 has an adhesive force. On the other hand, the surface of each protective sheet 70 on the opposite side from the cover main body 30 does not have an adhesive force for other sheets. Note that the adhesive force of each protective sheet 70 is such an adhesive force that the protective sheet 70 can be peeled off by fingers without breaking other sheets. Therefore, each protective sheet 70 is joined to the cover main body 30 and the elastic body 60 so as to be removable. The material of each protective sheet 70 is a synthetic resin and is, for example, PET or the like. In the present embodiment, the material of the protective sheet 70 is the same PET as the material of the first sheet 40.

Operation of Present Embodiment

When the cover 20 is attached to the occlusal force meter 10, first, the cover 20 is disposed such that the first sheet 40 is located on a lower side. Then, the projecting portion 56 of the second sheet 50 is grabbed and lifted upward. At this time, the lift-up portion 59 of the second sheet 50 is also lifted upward together with the movement of the projecting portion 56. When the lift-up portion 59 is lifted upward, a part of the first sheet 40 overlapping with the lower side of the lift-up portion 59 appears on the surface.

In addition, when the lift-up portion 59 is lifted upward, the entire second sheet 50 is lifted upward. At this time, the first sheet 40 may be lifted upward while overlapping with the second sheet 50. However, the first sheet 40 is attracted to the lower side by the adhesive force of the protective sheet 70 disposed on the lower side of the first sheet 40. As a result, even when the second sheet 50 is lifted upward, the first sheet 40 is not attracted to the upper side, the first sheet 40 and the second sheet 50 have an opening therebetween, and a space is formed.

Next, the occlusal force meter 10 is inserted into the inside from the space formed between the first sheet 40 and the second sheet 50. At this time, the pressure sensor 12 is placed on the first sheet 40 that is exposed through lifting of the lift-up portion 59, and the occlusal force meter 10 is inserted. Then, the occlusal force meter 10 is inserted until the leading end of the occlusal force meter 10 is located at the ends of the first sheet 40 and the second sheet 50 in the second negative direction Y2. In this state, when viewed in a direction orthogonal to the main surface of the pressure sensor 12, the pressure sensor 12 is covered with the elastic bodies 60. In addition, as illustrated in FIG. 1, the entire pressure sensor 12 and the entire arm 13 are covered with the cover 20. Note that before the occlusal force meter 10 is inserted into an oral cavity, each protective sheet 70 is removed from the cover main body 30 and the elastic body 60.

When the occlusal force is measured, the occlusal force meter 10 with the cover 20 attached is inserted into the oral cavity. Then, the pressure sensor 12 is bitten with teeth from above the elastic body 60 and the cover main body 30. Specifically, the pressure sensor 12 is bitten with teeth in a direction orthogonal to the main surface of each plate material 12A of the pressure sensor 12. The first resin material 12B of the pressure sensor 12 is deformed by receiving force. The deformation of the first resin material 12B changes the capacitance between the pair of plate materials 12A. The occlusal force meter 10 detects the change in the capacitance of the pressure sensor 12 as a change in pressure and outputs the change to the display 14 as an occlusal force.

Advantages of Present Embodiment (1) In the above embodiment, the cover main body 30 and the elastic bodies 60 cover the pressure sensor 12. The rubber hardness of the elastic bodies 60 is equal to or less then E15, which is appropriately small. Therefore, when the pressure sensor 12 is bitten during measurement of the occlusal force, the elastic bodies 60 act as a cushioning material and can reduce the impact on the teeth. That is, damage to the teeth can be reduced. In addition, the Young's modulus of the material of the cover main body 30 is larger than the Young's modulus of the material of the elastic bodies 60. Since the cover main body 30 has an appropriate hardness, the cover main body 30 is less likely to be damaged. Therefore, entry of saliva or the like into the cover main body 30 can be reduced when the occlusal force meter 10 is used.

(2) In the above embodiment, the outer surface of the cover main body 30 is more hydrophobic than the elastic bodies 60. Therefore, even if saliva adheres to the cover main body 30 when the occlusal force is measured, the cover main body 30 repels the saliva, and the saliva is likely to remain on the elastic bodies 60.

(3) In the above embodiment, the elastic bodies 60 are entirely made of a foamed resin. In addition, open cells connected to the outside of the elastic bodies 60 exist in the elastic bodies 60. Therefore, when the cover 20 is inserted into the mouth, the elastic bodies 60 can absorb the saliva. When the elastic bodies 60 absorb the saliva, the cover 20 becomes less slippery on the teeth when the pressure sensor 12 is bitten from above the cover 20.

(4) In the above embodiment, the length of the virtual line segment VL is greater than the maximum dimension L of each elastic body 60 in the direction along the virtual line segment VL. That is, when viewed in the direction along the first axis X, the dimension of the portion of the cover main body 30 protruding from each elastic body 60 along the second axis Y is larger than the dimension of each elastic body 60 in the direction along the second axis Y. According to the above dimensional relationship, even if the saliva adhering to the elastic bodies 60 reaches the cover main body 30, there is a considerable distance for the saliva to reach the opening edge of the cover main body 30. Therefore, the saliva is less likely to reach the opening edge of the cover main body 30, and entry of the saliva into the cover main body 30 can be reduced.

(5) In the above embodiment, the cover main body 30 is a flat bag without gussets in which a part of the peripheral edge of the first sheet 40 and a part of the peripheral edge of the second sheet 50 are joined to each other. Therefore, the cover main body 30 can be produced without resin molding or the like and can be efficiently produced. In addition, when the cover main body 30 is a flat bag without gussets, the cover 20 is not bulky when carried.

(6) In the above embodiment, the elastic bodies 60 cover the entire covered region R of the cover main body 30. That is, the edge of the covered region R is not exposed from the elastic bodies 60. Therefore, when the occlusal force meter 10 is used, the inside of the oral cavity can be prevented from being damaged due to contact of the edge of the covered region R with the inside of the oral cavity.

(7) In the above embodiment, the second sheet 50 includes the projecting portion 56. The projecting portion 56 projects toward the outside of the first sheet 40 from the edge 41 of the first sheet 40 in the plan view along an axis orthogonal to the first sheet 40. Therefore, by lifting the projecting portion 56, the cover main body 30 can be easily opened. That is, the cover 20 can be easily attached to the occlusal force meter 10.

(8) In the above embodiment, the second sheet 50 includes the lift-up portion 59. In addition, the entire lift-up portion 59 is not joined to the first sheet 40. As described above, when the projecting portion 56 is lifted, the lift-up portion 59 is lifted up together with the projecting portion 56. Then, the inner surface of the first sheet 40 is exposed. By inserting the occlusal force meter 10 along the exposed inner surface of the first sheet 40, the occlusal force meter 10 can be easily inserted into the cover main body 30.

(9) In the above embodiment, the lift-up portion 59 is the region between the two slits 58. Therefore, the lift-up portion 59 can be achieved by a simple method of forming the slits 58 in the second sheet 50. Therefore, when the lift-up portion 59 is provided in an existing cover main body 30, a significant design change is not needed.

(10) In the above embodiment, the protective sheets 70 are joined to the cover main body 30 and the elastic bodies 60 so as to be removable. The protective sheets 70 are peeled off from the cover main body 30 and the elastic bodies 60 during measurement. That is, the cover main body 30 and the elastic bodies 60 are protected by the protective sheets 70 before measurement, and dust and the like are less likely to adhere to the cover main body 30 and the elastic bodies 60.

(11) In the above embodiment, the projecting portion 56 has the through-hole 57. Since the edge of the through-hole 57 functions as a slip stopper when the projecting portion 56 is lifted, the projecting portion 56 can be easily lifted.

Modifications of Present Embodiment

The above embodiment can be implemented with the following modifications. The above embodiment and the following modifications can be combined with each other within a technically consistent range.

In the above embodiment, the shape of the occlusal force meter 10 is not limited to the example of the above embodiment. For example, the handle 11 may have a projection projecting from the outer surface of the handle 11. In addition, the projection is preferably set at a position where the projection can be inserted through the through-hole 57 of the second sheet 50 when the cover main body 30 is attached to the occlusal force meter 10. In this example, the cover main body 30 attached to the occlusal force meter 10 is less likely to come off.

In the above embodiment, the configuration of the pressure sensor 12 is not limited to the example of the above embodiment. For example, the pressure sensor 12 may be a diaphragm type pressure sensor that detects the pressure of a fluid by a pressure sensitive element with a diaphragm interposed therebetween, a gauge type pressure sensor using a strain sensor, or the like.

In the above embodiment, the outer surface of the cover main body 30 may be as hydrophobic as the elastic bodies 60 or less hydrophobic.

In the above embodiment, the shape of the elastic bodies 60 is not limited to the example of the above embodiment. For example, the elastic bodies 60 may have a circular shape in the plan view. In addition, the entire elastic bodies 60 may have a cap shape that covers the end portion of the cover main body 30 in the second negative direction Y2 and is fitted and attached to the cover main body 30.

In the above embodiment, the elastic bodies 60 may be provided on at least one of the first sheet 40 and the second sheet 50.

In the above embodiment, the elastic bodies 60 do not have to be made of only a foamed resin. For example, a resin film may be attached to the outer surface of the foamed resin. In addition, the elastic bodies 60 do not have to include a foamed resin as long as the rubber hardness of the elastic bodies 60 is equal to or less than E15.

In the above embodiment, in the cover 20, the length of the virtual line segment VL may be less than or equal to the maximum dimension L of each elastic body 60 in the same direction as the virtual line segment VL. For example, as long as another sheet is provided at the end portion of the cover main body 30 in the second positive direction Y1, saliva can be prevented from adhering to the pressure sensor 12 and the arm 13.

In the above embodiment, the shapes of the first sheet 40 and the second sheet 50 are not limited to the examples of the above embodiment. For example, the first sheet 40 and the second sheet 50 may have a square shape, a trapezoidal shape, a circular shape, or an elliptical shape. In addition, the overall dimension of one sheet may be larger than the other sheet. In addition, the first sheet 40 and the second sheet 50 may be folded so that the cover main body 30 has a bag shape with gussets.

In the above embodiment, the number of openings between the first sheet 40 and the second sheet 50 may be more than one. For example, the first sheet 40 and the second sheet 50 may be partially joined in the second negative direction Y2, the third positive direction Z1, and the third negative direction Z2, and a plurality of openings may be present between the jointed portions, as long as a bag shape is formed as a whole.

In the above embodiment, as long as the first sheet 40 and the second sheet 50 are disposed to face each other, the configuration of the cover main body 30 is not limited to the example of the above embodiment. For example, one sheet may be folded in two, and the fold line of the sheet may be used as a boundary to form the first sheet 40 and the second sheet 50. In this case, for example, by joining end portions of two unfolded sides of the sheet folded in two, the cover main body 30 having a bag shape is formed.

In the above embodiment, in the plan view along the first axis X, a part of the covered region R of the cover main body 30 may protrude from the elastic bodies 60. In the above embodiment, since both corner portions of the first sheet 40 and the second sheet 50 in the second negative direction Y2 are rounded, even if the corner portions of the cover main body 30 come into contact with the inside of the oral cavity, the inside of the oral cavity is less likely to be damaged.

In the above embodiment, the shape of the projecting portion 56 of the second sheet 50 is not limited to the example of the above embodiment. In addition, the projecting portion 56 does not have to have the through-hole 57.

In the above embodiment, the second sheet 50 does not have to have the projecting portion 56. For example, the shape of the second sheet 50 may coincide with the shape of the first sheet 40.

In the above embodiment, the extending dimensions of the two slits 58 do not have to coincide with each other.

In the above embodiment, the position and the shape of the lift-up portion 59 may be appropriately changed. For example, the second sheet 50 does not have to be provided with the slits 58, and the lift-up portion 59 may extend over the entire dimension of the base 55 along the third axis Z. In this case, as long as the edges of the lift-up portion 59 in the direction along the third axis Z are not joined to the first sheet 40, the lift-up portion 59 can be peeled off from the first sheet 40 and lifted. In addition, if the first sheet 40 and the second sheet 50 are properly opened when the projecting portion 56 is lifted, the lift-up portion 59 can be omitted.

In the above embodiment, in the plan view along the first axis X while the first sheet 40 is planar, as long as the slits 58 pass over the edge 41 of the first sheet 40, the number of the slits 58 may be one, or three or more. In this case, a region between the two adjacent slits 58 can function as the lift-up portion 59.

In the above embodiment, only a part of the surface of each protective sheet 70 facing the cover main body 30 may have an adhesive force. In addition, each protective sheet 70 does not have to be joined to the entire surface of the elastic body 60, and may be joined to at least a part of the elastic body 60.

In the above embodiment, the shape of each protective sheet 70 may be appropriately changed. The shape of each protective sheet 70 preferably covers portions of the cover main body 30 and the elastic body 60 in contact with the pressure sensor 12 during measurement. In addition, if covers 20 are stacked on top of each other before the measurement so that the covers 20 can be sanitarily stored, the protective sheets 70 can be omitted.

REFERENCE SIGNS LIST

10 occlusal force meter
11 handle
12 pressure sensor
13 arm
20 cover
30 cover main body
40 first sheet
50 second sheet
56 projecting portion
58 slit
59 lift-up portion
60 elastic body
70 protective sheet
L maximum dimension
VL virtual line segment

The invention claimed is:

1. A cover for an occlusal force meter, the cover comprising:

a cover main body that covers a pressure sensor of the occlusal force meter, the cover main body having a bag shape;

an elastic body attached to an outer surface of the cover main body; and a protective sheet that is removably joined to the elastic body on an opposite side of the elastic body from the cover main body, wherein a Young's modulus of a material of the cover main body is larger than a Young's modulus of a material of the elastic body, and a rubber hardness of the elastic body is equal to or less than E15.

2. The cover for an occlusal force meter according to claim 1, wherein the outer surface of the cover main body is more hydrophobic than the elastic body.

3. The cover for an occlusal force meter according to claim 2, wherein the elastic body includes a foamed resin, and the foamed resin includes open cells connected to an outside of the elastic body.

4. The cover for an occlusal force meter according to claim 1, wherein the elastic body includes a foamed resin, and the foamed resin includes open cells connected to an outside of the elastic body.

5. The cover for an occlusal force meter according to claim 1, wherein the cover main body includes a first sheet and a second sheet facing the first sheet, and in a plan view along an axis orthogonal to the first sheet while the first sheet is planar, when a shortest virtual line segment is drawn from the elastic body to an opening edge of the cover main body, a length of the virtual line segment is larger than a maximum dimension of the elastic body in a same direction as the virtual line segment.

6. The cover for an occlusal force meter according to claim 1, wherein the cover main body includes a first sheet and a second sheet facing the first sheet, and the cover main body is a flat bag without gussets in which a part of a peripheral edge of the first sheet and a part of a peripheral edge of the second sheet are joined to each other.

7. The cover for an occlusal force meter according to claim 1, wherein the cover main body includes a first sheet and a second sheet facing the first sheet, in a plan view along an axis orthogonal to the first sheet while the first sheet is planar, when a shortest virtual line segment is drawn from the elastic body to an opening edge of the cover main body, a positive direction is a direction along the virtual line segment toward the opening edge when viewed from the elastic body, and a negative direction is a direction opposite to the positive direction, and in the plan view, the elastic body covers an entire region of the cover main body on the negative direction side when viewed from an end of the elastic body in the positive direction.

8. The cover for an occlusal force meter according to claim 1, wherein the cover main body includes a first sheet and a second sheet facing the first sheet, and in a plan view along an axis orthogonal to the first sheet while the first sheet is planar, the second sheet includes a projecting portion projecting from an opening edge of the first sheet to an outside of the first sheet.

9. The cover for an occlusal force meter according to claim 8, wherein the second sheet includes a lift-up portion that is adjacent to the projecting portion in a direction opposite to a projecting direction of the projecting portion, and when an orthogonal axis is an axis along the second sheet and orthogonal to the projecting direction, the entire lift-up portion including opposed edges thereof in a direction along the orthogonal axis are not joined to the first sheet, and the lift-up portion is separable from the first sheet together with the projecting portion.

10. The cover for an occlusal force meter according to claim 9, wherein the second sheet has a slit extending from an outer edge of the second sheet at each side of the lift-up portion in a direction along the orthogonal axis, and in the plan view along an axis orthogonal to the first sheet while the first sheet is planar, the slit passes over the opening edge of the first sheet.

11. The cover for an occlusal force meter according to claim 1, wherein the elastic body is a first elastic body, and the cover further comprises:

a second elastic body attached to the outer surface of the cover main body at a location opposite to that of the first elastic body, wherein a Young's modulus of the material of the cover main body is larger than a Young's modulus of a material of the second elastic body, and a rubber hardness of the second elastic body is equal to or less than E15.

12. The cover for an occlusal force meter according to claim 11, wherein the first elastic body and the second elastic body have a same shape.

13. The cover for an occlusal force meter according to claim 11, wherein a material of the first elastic body and the second elastic body is a polyolefin-based resin.

14. The cover for an occlusal force meter according to claim 11, wherein the first elastic body and the second elastic body each include a foamed resin, and the foamed resin includes open cells connected to an outside of the first elastic body and the second elastic body, respectively.

15. The cover for an occlusal force meter according to claim 11, wherein the outer surface of the cover main body is more hydrophobic than each of the first elastic body and the second elastic body.

16. The cover for an occlusal force meter according to claim 1, wherein a material of the elastic body is a polyolefin-based resin.

17. A cover for an occlusal force meter, the cover comprising:

a cover main body that covers a pressure sensor of the occlusal force meter, the cover main body having a bag shape;

an elastic body attached to an outer surface of the cover main body:

a first protective sheet that is removably joined to the first elastic body on an opposite side of the first elastic body from the cover main body; and a second protective sheet that is removably joined to the second elastic body on an opposite side of the second elastic body from the cover main body, wherein a Young's modulus of a material of the cover main body is larger than a Young's modulus of a material of the elastic body, a rubber hardness of the elastic body is equal to or less than E15, and wherein the elastic body is a first elastic body, and the cover further comprises:

a second elastic body attached to the outer surface of the cover main body at a location opposite to that of the first elastic body, wherein a Young's modulus of the material of the cover main body is larger than a Young's modulus of a material of the second elastic body, and a rubber hardness of the second elastic body is equal to or less than E15.

\* \* \* \* \*